(12) United States Patent
Wang et al.

(10) Patent No.: US 12,202,874 B2
(45) Date of Patent: Jan. 21, 2025

(54) FUSION PROTEIN AND ITS PREPARATION METHOD FOR INTERMEDIATE POLYPEPTIDE OF SEMAGLUTIDE

(71) Applicant: NANJING HANXIN PHARMACEUTICAL TECHNOLOGY CO., LTD., Nanjing (CN)

(72) Inventors: Jing Wang, Nanjing (CN); Chuangen Tang, Nanjing (CN); Teng Zhang, Nanjing (CN); Xiaoyang Fan, Nanjing (CN); Bo Jin, Nanjing (CN)

(73) Assignee: NANJING HANXIN PHARMACEUTICAL TECHNOLOGY CO., LTD., Nanjing (CN)

( * ) Notice: Subject to any disclaimer, the term of this patent is extended or adjusted under 35 U.S.C. 154(b) by 0 days.

(21) Appl. No.: 18/755,691

(22) Filed: Jun. 27, 2024

(65) Prior Publication Data
US 2024/0343772 A1    Oct. 17, 2024

Related U.S. Application Data

(63) Continuation of application No. PCT/CN2022/140568, filed on Dec. 21, 2022.

(30) Foreign Application Priority Data

Dec. 31, 2021  (CN) .......................... 202111664146.2

(51) Int. Cl.
| | |
|---|---|
| C07K 14/605 | (2006.01) |
| C07K 7/06 | (2006.01) |
| C07K 14/00 | (2006.01) |
| C12N 1/20 | (2006.01) |
| C12P 21/02 | (2006.01) |
| C12R 1/19 | (2006.01) |

(52) U.S. Cl.
CPC .............. *C07K 14/605* (2013.01); *C07K 7/06* (2013.01); *C07K 14/001* (2013.01); *C12N 1/205* (2021.05); *C12P 21/02* (2013.01); *C12R 2001/19* (2021.05)

(58) Field of Classification Search
None
See application file for complete search history.

(56) References Cited

FOREIGN PATENT DOCUMENTS

| | | |
|---|---|---|
| CN | 107881187 A | 4/2018 |
| CN | 108191981 A | 6/2018 |
| CN | 109879970 A | 6/2019 |
| CN | 110128552 A | 8/2019 |
| CN | 113502296 A | 10/2021 |
| CN | 114292338 A | 4/2022 |
| WO | 2020182229 A1 | 9/2020 |

OTHER PUBLICATIONS

CN 110498849 translation provided by EPO (18 pages). (Year: 2019).*

* cited by examiner

*Primary Examiner* — Marsha Tsay
(74) *Attorney, Agent, or Firm* — IPRO, PLLC (57) ABSTRACT

The invention discloses a fusion protein and its preparation method for intermediate polypeptide of Semaglutide. The invention belongs to the technical field of genetic engineering and polypeptide preparation. The fusion protein comprises a fusion peptide, a protease cleavage site and a target main molecular sequence. By optimizing the fusion peptide sequence, changing the isoelectric point and hydrophilicity of the protein, the highest expression of the fusion protein is effectively increased to 13.1 g/L. Meanwhile, the properties of fusion protein are also improved, which is conducive to the development of subsequent extraction, enzyme digestion and purification processes. The yield of intermediate polypeptide after enzyme digestion is 3.62 g/L. The production cost of Semaglutide intermediate polypeptide Arg34GLP-1 (9-37) is reduced from the source, which is conducive to industrial scale-up and suitable for industrial production.

11 Claims, 2 Drawing Sheets
Specification includes a Sequence Listing.

FUSION PROTEIN AND ITS PREPARATION METHOD FOR INTERMEDIATE POLYPEPTIDE OF SEMAGLUTIDE

REFERENCE TO SEQUENCE LISTING

The instant application contains a Sequence Listing in XML format as a file named "3050-YGHY-2024-09-SEQ.xml", created on Sep. 18, 2024, of 17111 bytes in size, and which is hereby incorporated by reference in its entirety.

CROSS REFERENCE TO RELATED APPLICATIONS

This application is a 371 of International Application No. PCT/CN2022/140568, filed Dec. 11, 2022, which claims the priority benefit of China application no,202111664146.2 filed on Dec. 31, 2021. The entirety of each of the above mentioned patent applications is hereby incorporated by reference herein and made a part of this specifications.

TECHNICAL FIELD

The invention relates to a fusion protein and its preparation method for intermediate polypeptide of Semaglutide, in particular to a new fusion protein sequence that can efficiently prepare Semaglutide intermediate polypeptide Arg34GLP-1(9-37), which belongs to the technical field of genetic engineering and polypeptide preparation. polypeptide Arg34GLP-1(9-37) is reduced from the source, which is conducive to industrial scale-up and suitable for industrial production.

BACKGROUND

Type 2 diabetes mellitus (T2DM) is a chronic metabolic disorder syndrome caused by impaired function of human islet beta cells, insufficient insulin secretion or increased insulin resistance of target tissues. Clinically, it mainly presents symptoms such as polydipsia, polyphagia, polyuria and weight loss, and it also has the risk of complications such as sudden glycosuric ketoacidosis and hyperosmolar coma. T2DM is a chronic metabolic disease, most of which occurs after the age of 35~40, accounting for more than 90% of diabetes patients. At present, the clinical drugs for the treatment of diabetes are mainly concentrated in various types of insulin and four categories of oral hypoglycemic drugs. In order to allow diabetes patients to have more choices in treatment, some new diabetes drugs came into being in the early 21st century, such as glucagon-like peptide-1 (GLP-1) analogues, which are structurally modified on the basis of endogenous GLP-1. Endogenous GLP-1 is a kind of hypoglycemic hormone secreted by intestinal L cells, containing more than 30 amino acids. It can bind to GLP-1 receptors on the surface of cell membranes widely distributed in human heart, liver, kidney, pancreas, gastrointestinal tract and other organs, causing changes in related signal transduction pathways in cells, thereby exerting corresponding regulatory functions in the body. Therefore, GLP-1 has the characteristics of multi-function and multi-target action, especially the regulatory function of islet cells is particularly significant, and can promote insulin secretion according to the glucose level in the body. However, the only drawback is that GLP-1 is easily degraded by dipeptidyl peptidase IV in the human body, with a half-life of about 2 minutes, which limits its clinical use. The modified GLP-1 preparation not only retains the pharmacological effect of GLP-1, but also greatly improves the action time of the drug.

Semaglutide, a long-acting GLP-1 analogue developed by Novo Nordisk, is produced by yeast through gene recombination technology and is a weekly subcutaneous injection drug. As one of the representative drugs of GLP-1 analogs, Semaglutide has been shown in several clinical trials to effectively control blood glucose in combination with different oral hypoglycemic agents, and can reduce weight, systolic blood pressure and improve islet beta cell function in patients.

The main chain structure of Semaglutide is either a 29-amino acid intermediate polypeptide Arg34GLP-1(9-37) or a 27-amino acid intermediate polypeptide Arg34GLP-1(11-37). The amino acid sequence is EGTFTSDVSSYLEGQAAKEFIAWLVRGRG (SEQ ID NO:1) and TFTSDVSSYLEGQAAKEFIAWLVRGRG (SEQ ID NO:2), respectively. At present, the intermediate polypeptide is mainly prepared by chemical synthesis (the publication number of the patent is CN105753964A, published in 2016). However, there are many steps in the chemical process, a variety of organic solvents need to be used in the synthesis process and the amount of the organic solvents is large, which is not conducive to industrial amplification and is not friendly to the environment. The potential amino acid racemate impurities in the chemical synthesis of polypeptides bring some risks to the long-term use of the drug. Furthermore, there are some biological methods to prepare the intermediate polypeptide, include intracellular soluble expression, inclusion body expression and tandem expression of inclusion body form. Among them, intracellular soluble expression (the publication number of the patent is CN104745597A, published in 2015) has a low expression level and has no industrial amplification value. CN110498849A (published in 2019) related to inclusion body expression discloses a method for preparing the main peptide chain of Semaglutide with high purity and high yield, but the preferred leading peptide sequence KPSTYI disclosed is a short peptide sequence, which cannot effectively improve the expression level of fusion protein. In addition, patent CN111378027A (published in 2020) describes a tandem expression of the intermediate polypeptide of Semaglutide. KexII protease digestion site KR was used as linker, and the intermediate polypeptide of Semaglutide was obtained by the two-step enzyme digestion of KexII enzyme and carboxypeptidase B. The process is complicated and the price of KexII enzyme is expensive, and it does not have the significance of industrial amplification.

As technical problem from the above review, it is urgent to come up with a method of Semaglutide preparation with high fusion protein expression, simple process steps and suitable for industrial production.

SUMMARY

To solve the problems existing in Semaglutide preparation at present, the present invention discloses a fusion protein sequence that can efficiently prepare Semaglutide intermediate polypeptide Arg34GLP-1(9-37) or Arg34GLP-1(11-37). The fusion protein consists of a fusion peptide, the cleavage site of protease and the target main molecular sequence. The recombinant strain is constructed based on the E. coli expression system with clear genetic background, easy culture, and short fermentation time. By optimizing the fusion peptide sequence, changing the isoelectric point and hydrophilicity of the protein, the yield of the fusion protein is effectively increased. The fusion protein sequence is then digested to obtain the intermediate polypeptide Arg34GLP-1(9-37) or Arg34GLP-1(11-37) of Semaglutide. In order to realize the object of the invention, the technical scheme disclosed by the invention is as follows:

The first object of the invention is to provide a fusion peptide, and the amino acid sequence of fusion peptide is shown below:

(SEQ ID NO: 15)
MATKAVSVLKGDGPVQGIINFEQKESNGPVKVWGSIKGLTX₁GLHGFH

VHKX₂FVNQHLCGSHLVALYLVX₃;

X₁ is any amino acid selected from E or H;
X₂ is a permutation combination of any 0, 1, 2 or 3 of the W, L and V;
X₃ is a permutation combination of any 0, 1, or 2 of the H and A.

In one embodiment, the amino acid sequence of fusion peptide is any one of SEQ ID NO:3, SEQ ID NO:4, SEQ ID NO:5, SEQ ID NO:6, SEQ ID NO:7, SEQ ID NO:8, SEQ ID NO:9, SEQ ID NO:10 or SEQ ID NO:11, as following:

(SEQ ID NO: 3)
MATKAVSVLKGDGPVQGIINFEQKESNGPVKVWGSIKGLTEGLHGFHV

HKFVNQHLCGSHLVALYLV, (SEQ ID NO: 4)
MATKAVSVLKGDGPVQGIINFEQKESNGPVKVWGSIKGLTEGLHGFHV

HKFVNQHLCGSHLVALYLVHA, (SEQ ID NO: 5)
MATKAVSVLKGDGPVQGIINFEQKESNGPVKVWGSIKGLTHGLHGFHV

HKFVNQHLCGSHLVALYLV, (SEQ ID NO: 6)
MATKAVSVLKGDGPVQGIINFEQKESNGPVKVWGSIKGLTEGLHGFHV

HKFVNQHLCGSHLVALYLVH, (SEQ ID NO: 7)
MATKAVSVLKGDGPVQGIINFEQKESNGPVKVWGSIKGLTEGLHGFHV

HKWLVFVNQHLCGSHLVALYLVH, (SEQ ID NO: 8)
MATKAVSVLKGDGPVQGIINFEQKESNGPVKVWGSIKGLTHGLHGFHV

HKWLVFVNQHLCGSHLVALYLV, (SEQ ID NO: 9)
MATKAVSVLKGDGPVQGIINFEQKESNGPVKVWGSIKGLTHGLHGFHV

HKWLFVNQHLCGSHLVALYLV, (SEQ ID NO: 10)
MATKAVSVLKGDGPVQGIINFEQKESNGPVKVWGSIKGLTHGLHGFHV

HKWVFVNQHLCGSHLVALYLV, (SEQ ID NO: 11)
MATKAVSVLKGDGPVQGIINFEQKESNGPVKVWGSIKGLTHGLHGFHV

HKWFVNQHLCGSHLVALYLV.

The second object of the invention is to provide a fusion protein, comprising a fusion peptide described in claim 1. The fusion protein consists of fusion peptide-DDDDK-Arg34GLP-1(9-37) or fusion peptide-DDDDK-Arg34GLP-1(11-37); the amino acid sequence of DDDDK is shown as SEQ ID NO:16.

The amino acid sequence of Arg34GLP-1(9-37) is shown as SEQ ID NO:1.

The amino acid sequence of Arg34GLP-1(11-37) is shown as SEQ ID NO:2.

The third object of the invention is to provide a gene encoding the fusion peptide.

The fourth object of the invention is to provide a recombinant expression vector containing the gene encoding the fusion protein.

In one embodiment, the recombinant expression vectors comprises, but are not limited to, pET family, Duet family, pGEX family, pHY300, pHY300PLK, pPIC3K, pPIC9K, or pTrc family vectors.

In one embodiment, the pET family comprises pET-24a(+), pET-28a(+), pET-29a(+) and pET-30a(+). The Duet family comprises pRSFDuet-1 and pCDFDuet-1. The pTrc family comprises pTrc99a.

The fifth object of the invention is to provide a recombinant microbial cell that expresses the fusion protein, or contains a gene encoding the fusion protein.

In one embodiment, the host of the microbial cell includes, but is not limited to, *Escherichia coli* (*E. coli*), *Bacillus subtilis*, or *Pichia pastoris*.

In one embodiment, the *E. coli* includes *E. coli* JM109 (DE3), *E. coli* HMS174(DE3), *E. coli* BL21(DE3), *E. coli* Rostta2(DE3), *E. coli* Rostta gami(DE3), *E. coli* Rostta2 (DE3), *E. coli* DH5a, and *E. coli* W3110 and/or *E. coli* K12.

The sixth purpose of the invention is to provide a method for preparing the Semaglutide intermediate polypeptide Arg34GLP-1(9-37) or Arg34GLP-1(11-37). The recombinant microbial cell is used for fermentation to produce the Semaglutide intermediate polypeptide Arg34GLP-1(9-37) or Arg34GLP-1(11-37).

In one embodiment, the recombinant microbial cells are cultured at 35~40° C. for 10~12 h to obtain the seed solution, and then cultured in TB medium with the inoculum amount of 0.1%~2% (v/v) until the $OD_{600}$ value of the fermentation solution reached 6~8, and IPTG with a final concentration of 0.05~1 mM is added for induction. The fermentation is ended after induction for 14~18 h at 25~40° C. The intermediate polypeptide Arg34GLP-1(9-37) or Arg34GLP-1(11-37) of Semaglutideis obtained by homogenization of fermented cells, extraction, and enzyme digestion.

Preferably, the recombinant microbial cells are cultured at 37° C. for 12 h to obtain the seed solution, and then cultured in TB medium at 0.2% (v/v) inoculation rate until the $OD_{600}$; value of the fermentation solution reached 6-8, IPTG with a final concentration of 0.1 mM is added for induction, and the fermentation is ended after induction for 16 h at 37° C.

In one embodiment, the recombinant microbial cells are cultured in LB medium at 35~40° C. for 8~12 h to obtain pre-culture seeds solution, which is then transferred to the base fermentation medium for further 8~12 h to obtain seeds solution. The seed solution is transferred to the base fermentation medium for fermentation. When the value of $OD_{600}$ reached 100-200, IPTG with a final concentration of 0.05~1 mM is added for induction, and the fermentation is ended after induction for 8~18 h at 25~40° C., and the cells were collected. The intermediate polypeptide Arg34GLP-1 (9-37) or Arg34GLP-1(11-37) of Semaglutide is obtained by homogenization of fermented cells, extraction, and enzyme digestion.

Preferably, the recombinant microbial cells are cultured in LB medium at 37° C. for 8 h to obtain pre-culture seeds solution, which is then transferred to the base fermentation medium for further 8 h to obtain seeds solution. The seed solution is transferred to the 6 L base fermentation medium (BFM medium) for fermentation. When the value of $OD_{600}$ reachs 150, IPTG with a final concentration of 0.1 mM is added for induction, and the fermentation is ended after induction for 12 h at 37° C., and the cells are collected. The intermediate polypeptide Arg34GLP-1(9-37) or Arg34GLP-1(11-37) of Semaglutide is obtained by homogenization of fermented cells, extraction, and enzyme digestion.

In one embodiment, the inclusion bodies (IBs) precipitation is obtained by centrifuging and cellecting after lysing the fermented cells, and the IBs are washed with a washing buffer. The washed IBs are dissolved with dissolved buffer at a pH of 6.0~10.0 and a protein concentration of 5~55 g/L. Further preferably, the washed IBs are dissolved with dissolved buffer at a protein concentration of 20~30 g/L. The dissolved fusion protein is enzyme digested by enterokinase (EK) at 30~35° C. for 20~24 h to obtain the mixed solution containing intermediate polypeptide, fusion peptide and binding peptide. The mixed solution can be separated by ion exchange to obtain the intermediate polypeptide sample with the required purity. The purity of the purified Semaglutide intermediate polypeptide by HPLC was over 92.5%.

In one embodiment, the dissolved buffer is composed of 25 mM Tris, 0.1 mM EDTA-2Na, and the pH is adjusted to 7.5 to 8.0 to dissolve the IBs.

In one embodiment, the fermentation cells and the buffer are mixed with the volume ratio of 1:2, the cells are disrupted by high pressure homogenization, and the IBs precipitation is collected by centrifugation. The IBs precipitation is added to the washing buffer with the volume ratio of 1:2 for washing, and the washed IBs are added to the dissolution buffer at the protein concentration of 25 g/L for dissolution. After enzyme digestion of the dissolved fusion protein at 35° C. for 24 h, the mixed solution of intermediate polypeptide, fusion peptide and binding peptide could be obtained.

In one embodiment, the components of buffer used in homogenization are 25 mM Tris, 10 mM EDTA-2Na, and the buffer pH is 7.5 to 8.0.

In one embodiment, the composition of the washing buffer is 25 mM Tris, 0.25 M urea, 1% Tween 20, and the buffer pH is 7.5.

The invention provides an application of the fusion peptide, or the fusion protein, or the gene encoding the fusion protein, or the recombinant expression vector, or the microbial cell in the preparation of the Semaglutide intermediate polypeptide Arg34GLP-1(9-37).

The top three sequences of IBs yield performance are SEQ ID NO: 4, SEQ ID NO: 5 and SEQ ID NO: 11. It may because that the *E. coli* BL21 system is suitable for expression of neutral protein. Increasing the isoelectric point of fusion protein can effectively improve the expression efficiency of exogenous fusion protein in *E. coli*. However, when the isoelectric point is too high, it will also affect the expression efficiency of fusion protein. At the same time, the protein with high average hydrophilicity is easily dissolved in the supernatant during the extraction process, resulting in the loss of IBs extraction. Although the loss of IBs extraction can be reduced by reducing the average hydrophilicity of the fusion protein, too low average hydrophilicity and strong hydrophobicity will cause the fusion protein to be unable to be effectively translated and expressed in the intracellular system of *E. coli*. Therefore, when the average hydrophilicity of the fusion protein is controlled within a suitable range, a high IBs yield can be obtained.

Compared with the present technique, the invention has the following advantages:

(1) By changing the sequence of fusion peptide, the isoelectric point of fusion protein (fusion peptide-DDDDK-Arg34GLP-1 (9-37)) is increased, and the yield is significantly increased. Furthermore, a single step of enzyme digestion is needed, which can reduce the process steps. The yield and purity of the intermediate polypeptide are higher than that of the present technique; the amino acid sequence of DDDDK is shown as SEQ ID NO:16.

(2) The extraction and enzyme digestion yield are significantly improved by balancing the hydrophobicity of fusion protein and reducing the dissolution loss caused by hydrophilicity during IBs extraction, which can reduce the cost, and facilitate industrial amplification.

(3) The yield of the fusion protein prepared by the invention can reach up to 13.1 g/L, the crude content of the Semaglutide intermediate polypeptide after enzyme digestion can reach 3.62 g/L, the purity after purification can reach 92.5%, and the yield is greater than 86.2%.

DETAILED DESCRIPTION

In order to facilitate those skilled in the art to understand the present invention, the technical scheme of the invention will be further described in combination with specific embodiments below. However, the following contents shall not limit the scope of protection requested by the claims of the invention in any way.

Materials, reagents, etc. used in the following embodiments are all commercially available unless otherwise specified.

BFM-Medium: Diammonium hydrogen phosphate 6 g/L, ammonium chloride 4 g/L, potassium dihydrogen phosphate 13.5 g/L, magnesium sulfate 7 hydrate 1.39 g/L, citric acid 1 hydrate 2.8 g/L, yeast powder (Angie 802) 3 g/L, trace elements (large intestine) 10 mL/L, pH was adjusted to 7.0 with 10 M NaOH.

Example 1: Construction of Recombinant Strain Expressing Semaglutide Intermediate Polypeptide Fusion Protein Designed a fusion protein sequence for expression in *E. coli*: fusion peptide-DDDDK-Arg34GLP-1 (9-37); the amino acid sequence of DDDDK is shown as SEQ ID NO:16.

The fusion peptide not only can improve protein expression in the host, but also can protect the intermediate polypeptide Arg34GLP-1(9-37) from internal degradation during synthesis in the *E. coli*. The amino acid sequence of fusion peptide was MATKAVSVLKGDGPVQGIINFEQKESNGPVKVWGSIKGLTEGLHGFHVHKFVNQHLCGSHLVALYLV (SEQ ID NO: 3). The C-terminal of the fusion peptide sequence was connected to the intermediate polypeptide Arg34GLP-1(9-37) of Semaglutide through a DDDDK residue (SEQ ID NO:16).

Therefore, the complete amino acid sequence of fusion protein was MATKAVSVLKGDGPVQGIINFEQKESNGPVKVWGSIKGLTEGLHGFHVHKFVNQHLCGSHLVALYLVDDDD KEGTFTSDVSSYLEGQAAKEFIAWLVRGRG (SEQ ID NO:12), the isoelectric point (pI) of the fusion protein was 6.2, and the mean hydrophilicity was 0.

Figure 1:
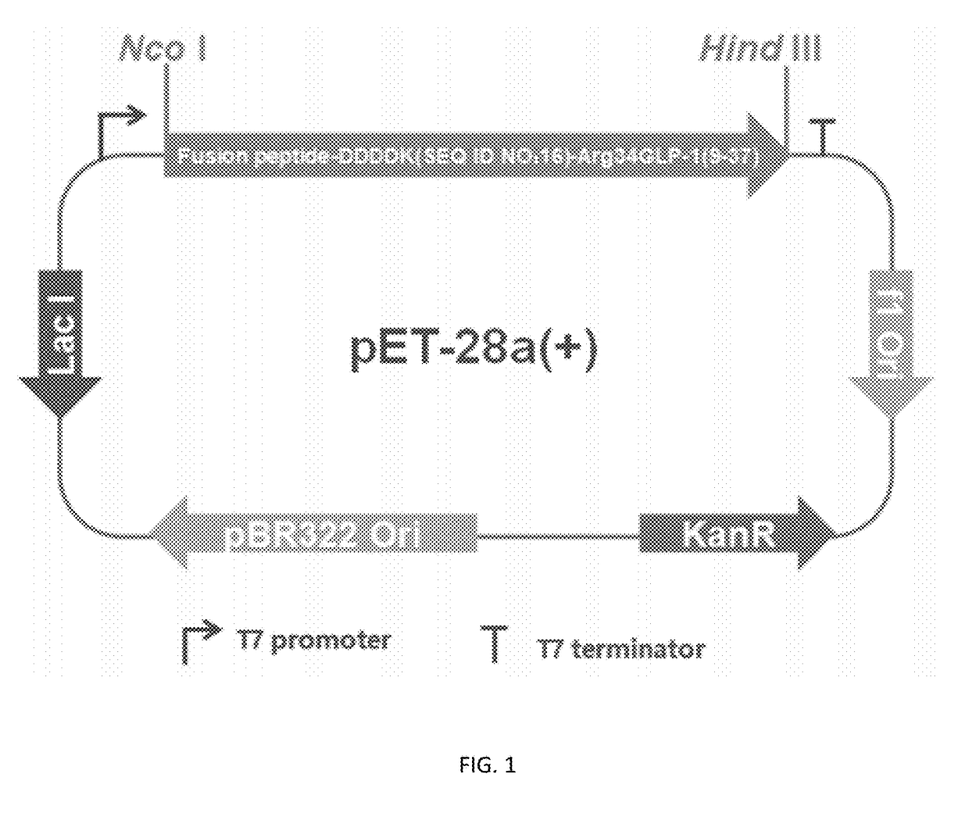
FIG. 1 is the schematic diagram of the construction of recombinant plasmid in Example 1.

The nucleotide sequence encoding the fusion protein was synthesized by PCR technology, and the obtained nucleic acid sequence was inserted into the corresponding enzyme cleavage site of plasmid pET-28a(+) through the Nco I/Hind III site. The recombinant plasmid map was shown in FIG. 1. The recombinant plasmid was transferred to host *E. coli* BL21(DE3), and recombinant strain S1 expressing the intermediate polypeptide fusion protein of Semaglutide was obtained.

Example 2: Expression of Semaglutide Intermediate Polypeptide Fusion Protein in Shaker System Culture the recombinant strain S1 of Example 1 in LB media at 37° C. for 12 h to recover the seeds solution. The recovered seeds solution were inoculated into TB media with 0.2% (v/v) inoculation amount. When the cell concentration reaches O.D. (optical density) 600 nm of about 6-8, IPTG with a final concentration of 0.1 mM was added for induction. Induce for another 16 h at 37° C. to finish the fermentation. The cells were collected by centrifugation.

Example 3: Yield Detection of Semaglutide Intermediate Polypeptide Fusion Protein Expression in Shaker System The fermentation cells of Example 2 were washed and disrupted by ultrasonic cell disruptor. The IBs were collected by centrifugating the disrupted suspension. The whole cells and IBs were detected by SDS-PAGE, and the purity of target protein was detected by optical densitometer. At the same time, BCA kit was used to detect the total protein content of whole cells and IBs. The expression of intermediate polypeptide fusion protein was obtained by multiplying the total protein amount and electrophoretic purity. The yield of fusion protein from recombinant strain S1 after fermentation and induction was 1.56 g/L, and 0.95 g/L IBs were obtained after disruption and washing.

Example 4: Construction of Recombinant Strain and Expression of Semaglutide Intermediate Polypeptide Fusion Protein in Shaker System The amino acid sequence of fusion peptide was shown as SEQ ID NO: 4. The C-terminal of the fusion peptide sequence was connected to the intermediate polypeptide Arg34GLP-1(9-37) of Semaglutide through a DDDDK residue (SEQ ID NO:16). The complete fusion protein contained the fusion peptide sequence of SEQ ID NO: 4, the isoelectric point (pI) of the fusion protein was 6.4, and the mean hydrophilicity was 0. The recombinant strain S2 was constructed according to the operation of Example 1, and the fusion protein was expressed according to the operation of Example 2 and Example 3. The yield of fusion protein from recombinant strain S2 after fermentation and induction was 1.44 g/L, and 1.32 g/L IBs were obtained after disruption and washing.

Example 5: Construction of Recombinant Strain and Expression of Semaglutide Intermediate Polypeptide Fusion Protein in Shaker System The amino acid sequence of fusion peptide was shown as SEQ ID NO: S. The C-terminal of the fusion peptide sequence was connected to the intermediate polypeptide Arg34GLP-1(9-37) of Semaglutide through a DDDDK residue(SEQ ID NO:16). The complete fusion protein contained the fusion peptide sequence of SEQ ID NO: 5, the isoelectric point (pI) of the fusion protein was 6.7, and the mean hydrophilicity was 0. The recombinant strain S3 was constructed according to the operation of Example 1, and the fusion protein was expressed according to the operation of Example 2 and Example 3. The yield of fusion protein from recombinant strain S3 after fermentation and induction was 1.73 g/L, and 1.43 g/L IBs were obtained after disruption and washing.

Example 6: Construction of Recombinant Strain and Expression of Semaglutide Intermediate Polypeptide Fusion Protein in Shaker System The amino acid sequence of fusion peptide was shown as SEQ ID NO: 6. The C-terminal of the fusion peptide sequence was connected to the intermediate polypeptide Arg34GLP-1(9-37) of Semaglutide through a DDDDK residue. The complete fusion protein contained the fusion peptide sequence of SEQ ID NO: 6, the isoelectric point (pI) of the fusion protein was 6.4, and the mean hydrophilicity was 0. The recombinant strain S4 was constructed according to the operation of Example 1, and the fusion protein was expressed according to the operation of Example 2 and Example 3. The yield of fusion protein from recombinant strain S4 after fermentation and induction was 1.36 g/L, and 1.17 g/L IBs were obtained after disruption and washing.

Example 7: Construction of Recombinant Strain and Expression of Semaglutide Intermediate Polypeptide Fusion Protein in Shaker System The amino acid sequence of fusion peptide was shown as SEQ ID NO: 7. The C-terminal of the fusion peptide sequence was connected to the intermediate polypeptide Arg34GLP-1(9-37) of Semaglutide through a DDDDK residue(SEQ ID NO:16). The complete fusion protein contained the fusion peptide sequence of SEQ ID NO: 7, and the isoelectric point (pI) of the fusion protein was 6.4, and the mean hydrophilicity was −0.1. The recombinant strain S5 was constructed according to the operation of Example 1, and the fusion protein was expressed according to the operation of Example 2 and Example 3. The yield of fusion protein from recombinant strain S5 after fermentation and induction was 0.93 g/L, and 0.87 g/L IBs were obtained after disruption and washing.

Example 8: Construction of Recombinant Strain and Expression of Semaglutide Intermediate Polypeptide Fusion Protein in Shaker System The amino acid sequence of fusion peptide was shown as SEQ ID NO: 8. The C-terminal of the fusion peptide sequence was connected to the intermediate polypeptide Arg34GLP-1(9-37) of Semaglutide through a DDDDK residue(SEQ ID NO:16). The complete fusion protein contained the fusion peptide sequence of SEQ ID NO: 8, and the isoelectric point (pI) of the fusion protein was 6.7, and the mean hydrophilicity was −0.1. The recombinant strain S6 was constructed according to the operation of Example 1, and the fusion protein was expressed according to the operation of Example 2 and Example 3. The yield of fusion protein from recombinant strain S6 after fermentation and induction was 1.16 g/L, and 1.08 g/L IBs were obtained after disruption and washing.

Example 9: Construction of Recombinant Strain and Expression of Semaglutide Intermediate Polypeptide Fusion Protein in Shaker System The amino acid sequence of fusion peptide was shown as SEQ ID NO: 9. The C-terminal of the fusion peptide sequence was connected to the intermediate polypeptide Arg34GLP-1(9-37) of Semaglutide through a DDDDK residue(SEQ ID NO:16). The complete fusion protein contained the fusion peptide sequence of SEQ ID NO: 9, and the isoelectric point (pl) of the fusion protein was 6.7, and the mean hydrophilicity was −0.1. The recombinant strain S7 was constructed according to the operation of Example 1, and the fusion protein was expressed according to the operation of Example 2 and Example 3. The yield of fusion protein from recombinant strain S7 after fermentation and induction was 1.24 g/L, and 1.14 g/L IBs were obtained after disruption and washing.

Example 10: Construction of Recombinant Strain and Expression of Semaglutide Intermediate Polypeptide Fusion Protein in Shaker System The amino acid sequence of fusion peptide was shown as SEQ ID NO: 10. The C-terminal of the fusion peptide sequence was connected to the intermediate polypeptide Arg34GLP-1(9-37) of Semaglutide through a DDDDK residue(SEQ ID NO:16). The complete fusion protein contained the fusion peptide sequence of SEQ ID NO: 10, and the isoelectric point (pl) of the fusion protein was 6.7, and the mean hydrophilicity was −0.1. The recombinant strain S8 was constructed according to the operation of Example 1, and the fusion protein was expressed according to the operation of Example 2 and Example 3. The yield of fusion protein from recombinant strain S8 after fermentation and induction was 1.15 g/L, and 1.04 g/L IBs were obtained after disruption and washing.

Example 11: Construction of Recombinant Strain and Expression of Semaglutide Intermediate Polypeptide Fusion Protein in Shaker System The amino acid sequence of fusion peptide was shown as SEQ ID NO: 11. The C-terminal of the fusion peptide sequence was connected to the intermediate polypeptide Arg34GLP-1(9-37) of Semaglutide through a DDDDK residue(SEQ ID NO:16). The complete fusion protein contains the fusion peptide sequence of SEQ ID NO: 11, and the isoelectric point (pl) of the fusion protein was 6.7, and the mean hydrophilicity was 0. The recombinant strain S9 was constructed according to the operation of Example 1, and the fusion protein was expressed according to the operation of Example 2 and Example 3. The yield of fusion protein from recombinant strain S9 after fermentation and induction was 1.45 g/L, and 1.25 g/L IBs were obtained after disruption and washing.

Example 12: Construction of Recombinant Strain Xpressing Semaglutide Intermediate Polypeptide Fusion Protein Designed a fusion protein sequence for expression in *E. coli*: fusion peptide-DDDDK-Arg34GLP-1 (11-37); the amino acid sequence of DDDDK is shown as SEQ ID NO:16.

The fusion peptide not only can improve protein expression in the host, but also can protect the intermediate polypeptide Arg34GLP-1(11-37) from internal degradation during synthesis in the *E. coli*. The amino acid sequence of fusion peptide was MATKAVSVLKGDGPVQGIIN-FEQKESNGPVKVWGSIKGLTEGLHGFHVHKFVNQH-LCGSHLVALYLVHA (SEQ ID NO:4). The C-terminal of the fusion peptide sequence was connected to the intermediate polypeptide Arg34GLP-1(11-37) of Semaglutide through a DDDDK residue(SEQ ID NO:16). Therefore, the complete amino acid sequence of fusion protein was MATKAVSVLKGDGPVQGIIN-FEQKESNGPVKVWGSIKGLTEGLHGFHVHKFVNQH-LCGSHLVALYLVHA<u>DD DDK</u>TFTSDVSSYLEGQ-AAKEFIAWLVRGRG (SEQ ID NO:13) the isoelectric point (pl) of the fusion protein was 6.7, and the mean hydrophilicity was 0.

The recombinant strain S10 was constructed according to the operation of Example 1, and the fusion protein was expressed according to the operation of Example 2 and Example 3. The yield of fusion protein from recombinant strain S10 after fermentation and induction was 1.69 g/L, and 1.40 g/L IBs were obtained after disruption and washing.

Example 13: Construction of Recombinant Strain and Expression of Semaglutide Intermediate Polypeptide Fusion Protein in Shaker System The amino acid sequence of fusion peptide was shown as SEQ ID NO: 5. The C-terminal of the fusion peptide sequence was connected to the intermediate polypeptide Arg34GLP-1(11-37) of Semaglutide through a DDDDK residue(SEQ ID NO:16). The complete fusion protein contained the fusion peptide sequence of SEQ ID NO: 5, and the isoelectric point (pi) of the fusion protein was 7.6, and the mean hydrophilicity was 0.1. The recombinant strain S11 was constructed according to the operation of Example 1, and the fusion protein was expressed according to the operation of Example 2 and Example 3. The yield of fusion protein from recombinant strain S11 after fermentation and induction was 1.17 g/L, and 1.11 g/L IBs were obtained after disruption and washing.

Example 14: Construction of Recombinant Strain and Expression of Semaglutide Intermediate Polypeptide Fusion Protein in Shaker System The amino acid sequence of fusion peptide was shown as SEQ ID NO: 11. The C-terminal of the fusion peptide sequence was connected to the intermediate polypeptide Arg34GLP-1(11-37) of Semaglutide through a DDDDK residue(SEQ ID NO:16). The complete fusion protein contained the fusion peptide sequence of SEQ ID NO: 11, and the isoelectric point (pl) of the fusion protein was 7.6, and the mean hydrophilicity was 0.1. The recombinant strain S12 was constructed according to the operation of Example 1, and the fusion protein was expressed according to the operation of Example 2 and Example 3. The yield of fusion protein from recombinant strain S12 after fermentation and induction was 1.21 g/L, and 1.13 g/L IBs were obtained after disruption and washing. The results of the above examples were summarized in Table 1 below.

TABLE 1

| Recombinant strain | Sequence of fusion petide | pI | Mean Hydro-philicity | Yield of fusion protein(g/L) | Yield of IBs(g/L) |
|---|---|---|---|---|---|
| S1 | SEQ ID NO: 3 | 6.2 | 0 | 1.56 | 0.95 |
| S2 | SEQ ID NO: 4 | 6.4 | 0 | 1.44 | 1.32 |
| S3 | SEQ ID NO: 5 | 6.7 | 0 | 1.73 | 1.43 |
| S4 | SEQ ID NO: 6 | 6.4 | 0 | 1.36 | 1.17 |
| S5 | SEQ ID NO: 7 | 6.4 | −0.1 | 0.93 | 0.87 |
| S6 | SEQ ID NO: 8 | 6.7 | −0.1 | 1.16 | 1.08 |
| S7 | SEQ ID NO: 9 | 6.7 | −0.1 | 1.24 | 1.14 |
| S8 | SEQ ID NO: 10 | 6.7 | −0.1 | 1.15 | 1.04 |
| S9 | SEQ ID NO: 11 | 6.7 | 0 | 1.45 | 1.25 |
| S10 | SEQ ID NO: 4 | 6.7 | 0 | 1.69 | 1.4 |
| S11 | SEQ ID NO: 5 | 7.6 | −0.1 | 1.17 | 1.11 |
| S12 | SEQ ID NO: 11 | 7.6 | −0.1 | 1.21 | 1.13 |

Example 15: Fermentation of Recombinant Strain in Fermentor System

Cultured the recombinant strain S3 of Example 1 in LB media at 37° C. for 8 h to recover the pre-culture seeds solution. The recovered seeds were inoculated into BFM media to further culture for another 8 hours to obtain seeds solution, which was then inoculated into fermentor containing BFM media with a volume of 6 L. When the O.D. (optical density, 600 nm) value of the fermentation solution reached 150, IPTG with a final concentration of 0.1 mM was added for induction. Induce for another 12 h at 37° C. to finish the fermentation. The cells were collected by centrifugation.

Example 16: Extraction and Enzyme Digestion of Semaglutide Intermediate Polypeptide Fusion Protein The harvested cells in Example 15 were diluted with buffer at a volume ratio of 1:2 (that is, the cells from 1 L fermentation were diluted by 2 L buffer). The buffer contains 25 mM Tris, 10 mM EDTA-2Na, and pH was 7.5~8.0. The IBs precipitation was obtained by centrifugation after homogenization of cells, and washed with washing buffer at a volume ratio of 1:2 (that was, the IBs precipitation from 1 L fermentation were washed by 2 L washing buffer). The washing buffer contained 25 mM Tris, 0.25 M urea, 1% Tween 20, and pH was 7.5. The washing operation of IBs precipitation was repeated once. The washed IBs were dissolved by dissolved buffer at a protein concentration of 25 g/L. The dissolved buffer contained 25 mM Tris, 0.1 mM EDTA-2Na, and pH was adjusted to 7.5~8.0 for 0.5 h dissolution. The dissolved fusion protein was enzyme digested by enterokinase (EK) at 35° C. for 24 h to obtain the mixed solution containing intermediate polypeptide, fusion peptide, and binding peptide. The yield of fusion protein was 13.1 g/L and the yield of digested intermediate polypeptide was 3.62 g/L by HPLC.

Example 17: Expression of Semaglutide Intermediate Polypeptide Fusion Protein in Fermentor System The recombinant strain S2 of Example 4 was fermented, induced, extracted and enzyme digested according to the operation of Example 15 and Example 16. The yield of fusion protein was 11.4 g/L and the yield of digested intermediate polypeptide was 3.08 g/L by HPLC.

Example 18: Expression of Semaglutide Intermediate Polypeptide Fusion Protein in Fermentor System The recombinant strain S9 of Example 11 was fermented, induced, extracted and enzyme digested according to the operation of Example 15 and Example 16. The yield of fusion protein was 10.3 g/L and the yield of digested intermediate polypeptide was 2.77 g/L by HPLC.

Example 19: Purification of Semaglutide Intermediate Polypeptide

Figure 2:
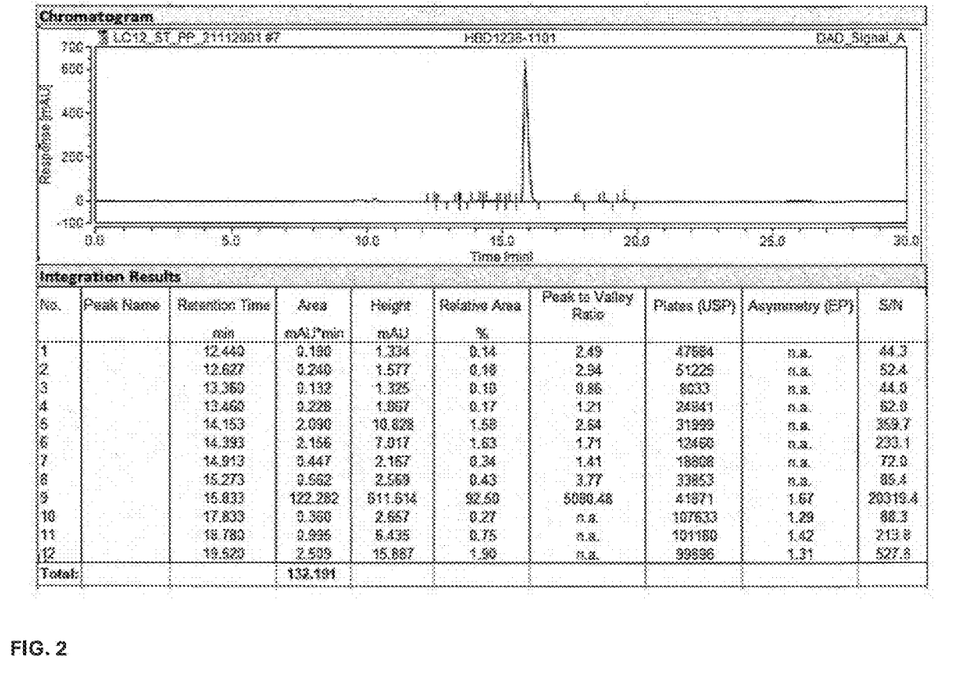
FIG. 2 is the HPLC chromatogram of main peak of ion exchange purification in Example 19.

The mixture solution containing 20.3 g target protein obtained in Example 16 was purified by ion exchange, and the washing peak 1, main peak and regeneration peak were obtained in turn. The main peak sample was taken for HPLC, and the elution time of HPLC was 15.833 min. As shown in FIG. 2, the purity of target protein was 92.5%. The sample of Semaglutide intermediate polypeptide collected was 17.5 g and the yield was 86.2%.

Comparative Example 1

Using the fusion peptide sequence published at present, which was similar to the fusion peptide sequence from this invention. The fusion peptide was used as leading peptide, and the sequence was MATHAVSVLKGDGPVQGIIN-FEQHESNGPVKVWGSIHGL TEGLHGFHVHKFVNQHLCGSHLVALYLV(SEQ ID NO:14). The recombinant strain S13 was constructed and the fusion protein was expressed according to the operation of Example 1~3. The yield of fusion protein from recombinant strain S13 after fermentation and induction was 0.85 g/L, and 0.61 g/L IBs were obtained after disruption and washing. The recombinant strain S13 was fermented, induced, extracted and enzyme digested according to the operation of Example 15 and Example 16. The yield of fusion protein was 6.5 g/L and the yield of digested intermediate polypeptide was 1.75 g/L by HPLC. Using the fusion peptide sequence in the invention, the yield of the intermediate polypeptide after enzyme digestion was 2.77~3.62 g/L, which was higher than the data in the comparative example.

The lead peptide sequences used in Liraglutide intermediate polypeptides preparation in this invention were not applicable to all GLP-1, such as the Semaglutide.

Although the present invention has been disclosed in terms of preferred embodiments, it is not intended to limit the present invention, and any person familiar with this technology can make various changes and modifications without departing from the spirit and scope of the present invention, so the scope of protection of the present invention shall be determined by the claims.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

SEQUENCE LISTING

```
Sequence total quantity: 16
SEQ ID NO: 1                    moltype = AA   length = 29
FEATURE                         Location/Qualifiers
source                          1..29
                                mol_type = protein
                                organism = synthetic construct
SEQUENCE: 1
EGTFTSDVSS YLEGQAAKEF IAWLVRGRG                                          29

SEQ ID NO: 2                    moltype = AA   length = 27
FEATURE                         Location/Qualifiers
source                          1..27
                                mol_type = protein
                                organism = synthetic construct
SEQUENCE: 2
TFTSDVSSYL EGQAAKEFIA WLVRGRG                                            27

SEQ ID NO: 3                    moltype = AA   length = 67
FEATURE                         Location/Qualifiers
source                          1..67
                                mol_type = protein
                                organism = synthetic construct
SEQUENCE: 3
MATKAVSVLK GDGPVQGIIN FEQKESNGPV KVWGSIKGLT EGLHGFHVHK FVNQHLCGSH         60
LVALYLV                                                                  67

SEQ ID NO: 4                    moltype = AA   length = 69
FEATURE                         Location/Qualifiers
source                          1..69
                                mol_type = protein
                                organism = synthetic construct
SEQUENCE: 4
MATKAVSVLK GDGPVQGIIN FEQKESNGPV KVWGSIKGLT EGLHGFHVHK FVNQHLCGSH         60
LVALYLVHA                                                                69

SEQ ID NO: 5                    moltype = AA   length = 67
FEATURE                         Location/Qualifiers
source                          1..67
                                mol_type = protein
                                organism = synthetic construct
SEQUENCE: 5
MATKAVSVLK GDGPVQGIIN FEQKESNGPV KVWGSIKGLT HGLHGFHVHK FVNQHLCGSH         60
LVALYLV                                                                  67

SEQ ID NO: 6                    moltype = AA   length = 68
FEATURE                         Location/Qualifiers
source                          1..68
                                mol_type = protein
                                organism = synthetic construct
SEQUENCE: 6
MATKAVSVLK GDGPVQGIIN FEQKESNGPV KVWGSIKGLT EGLHGFHVHK FVNQHLCGSH         60
LVALYLVH                                                                 68

SEQ ID NO: 7                    moltype = AA   length = 71
FEATURE                         Location/Qualifiers
source                          1..71
                                mol_type = protein
                                organism = synthetic construct
SEQUENCE: 7
MATKAVSVLK GDGPVQGIIN FEQKESNGPV KVWGSIKGLT EGLHGFHVHK WLVFVNQHLC         60
GSHLVALYLV H                                                             71

SEQ ID NO: 8                    moltype = AA   length = 70
FEATURE                         Location/Qualifiers
source                          1..70
                                mol_type = protein
                                organism = synthetic construct
SEQUENCE: 8
MATKAVSVLK GDGPVQGIIN FEQKESNGPV KVWGSIKGLT HGLHGFHVHK WLVFVNQHLC         60
GSHLVALYLV                                                               70

SEQ ID NO: 9                    moltype = AA   length = 69
FEATURE                         Location/Qualifiers
source                          1..69
                                mol_type = protein
                                organism = synthetic construct
```

```
SEQUENCE: 9
MATKAVSVLK GDGPVQGIIN FEQKESNGPV KVWGSIKGLT HGLHGFHVHK WLFVNQHLCG    60
SHLVALYLV                                                            69

SEQ ID NO: 10           moltype = AA  length = 69
FEATURE                 Location/Qualifiers
source                  1..69
                        mol_type = protein
                        organism = synthetic construct
SEQUENCE: 10
MATKAVSVLK GDGPVQGIIN FEQKESNGPV KVWGSIKGLT HGLHGFHVHK WVFVNQHLCG    60
SHLVALYLV                                                            69

SEQ ID NO: 11           moltype = AA  length = 68
FEATURE                 Location/Qualifiers
source                  1..68
                        mol_type = protein
                        organism = synthetic construct
SEQUENCE: 11
MATKAVSVLK GDGPVQGIIN FEQKESNGPV KVWGSIKGLT HGLHGFHVHK WFVNQHLCGS    60
HLVALYLV                                                             68

SEQ ID NO: 12           moltype = AA  length = 101
FEATURE                 Location/Qualifiers
source                  1..101
                        mol_type = protein
                        organism = synthetic construct
SEQUENCE: 12
MATKAVSVLK GDGPVQGIIN FEQKESNGPV KVWGSIKGLT EGLHGFHVHK FVNQHLCGSH    60
LVALYLVDDD DKEGTFTSDV SSYLEGQAAK EFIAWLVRGR G                        101

SEQ ID NO: 13           moltype = AA  length = 101
FEATURE                 Location/Qualifiers
source                  1..101
                        mol_type = protein
                        organism = synthetic construct
SEQUENCE: 13
MATKAVSVLK GDGPVQGIIN FEQKESNGPV KVWGSIKGLT EGLHGFHVHK FVNQHLCGSH    60
LVALYLVHAD DDDKTFTSDV SSYLEGQAAK EFIAWLVRGR G                        101

SEQ ID NO: 14           moltype = AA  length = 67
FEATURE                 Location/Qualifiers
source                  1..67
                        mol_type = protein
                        organism = synthetic construct
SEQUENCE: 14
MATHAVSVLK GDGPVQGIIN FEQHESNGPV KVWGSIHGLT EGLHGFHVHK FVNQHLCGSH    60
LVALYLV                                                              67

SEQ ID NO: 15           moltype = AA  length = 69
FEATURE                 Location/Qualifiers
source                  1..69
                        mol_type = protein
                        organism = synthetic construct
SITE                    41
                        note = X is any amino acid selected from E or H
SITE                    51
                        note = X is a permutation combination of any 0, 1, 2 or 3
                         of the W, L and V
SITE                    69
                        note = X is a permutation combination of any 0, 1, or 2 of
                         the H and A
SEQUENCE: 15
MATKAVSVLK GDGPVQGIIN FEQKESNGPV KVWGSIKGLT XGLHGFHVHK XFVNQHLCGS    60
HLVALYLVX                                                            69

SEQ ID NO: 16           moltype = AA  length = 5
FEATURE                 Location/Qualifiers
source                  1..5
                        mol_type = protein
                        organism = synthetic construct
SEQUENCE: 16
DDDDK                                                                5
```

What is claimed is:

1. A fusion peptide comprising the amino acid sequence of SEQ ID NO: 5.

2. A fusion protein comprising:
the fusion peptide of claim 1, and
the amino acid residues DDDDK (SEQ ID NO: 16) attached to
Arg34GLP-1(9-37) (SEQ ID NO: 1) or Arg34GLP-1(11-37) (SEQ ID NO: 2).

3. A nucleic acid sequence encoding the fusion protein of claim 2.

4. A recombinant expression vector comprising the nucleic acid sequence of claim 3.

5. The recombinant expression vector of claim 4, wherein the recombinant expression vector is a pET vector, a Duet vector, a pGEX vector, a pHY300 vector, a pHY300PLK vector, a pPIC3K vector, a pPIC9K vector, or a pTrc vector;
wherein the pET vector is selected from pET-24a(+), pET-28a(+), pET-29a(+), and pET-30a(+);
wherein the Duet vector is selected from pRSFDuet™-1 and pCDFDuet™-1; and
wherein the pTrc vector is pTrc99a.

6. A recombinant microbial cell comprising the recombinant expression vector of claim 4, wherein the cell is *Escherichia coli, Bacillus subtilis,* or *Pichia pastoris.*

7. The recombinant microbial cell of claim 6, wherein the cell is *Escherichia coli* selected from *E. coli* JM109(DE3), *E. coli* HMS174(DE3), *E. coli* BL21(DE3), *E. coli* E Rosetta™2(DE3), *E. coli* Rosetta-gami™ (DE3), *E. coli* DH5a, *E. coli* W3110, and/or *E. coli* K12.

8. A method of preparing Semaglutide intermediate polypeptide Arg34GLP-1(9-37) (SEQ ID NO: 1), comprising:
fermenting the recombinant microbial cell of claim 7 in a fermentation solution to produce Semaglutide intermediate polypeptide Arg34GLP-1(9-37) (SEQ ID NO: 1).

9. The method of claim 8, further comprising:
culturing the recombinant microbial cell at 35° F. to 40° C. for 10 to 12 hours to obtain a seed solution,
culturing a fermentation solution with 0.1% (v/v) to 2% (v/v) of the seed solution in TB medium until an $OD_{600}$ value of the fermentation solution reaches 6 to 8,
inducing the fermentation solution by adding IPTG at a concentration of 0.05 mM to 1 mM,
incubating the fermentation solution for 14 to 18 hours at 25° C. to 40° C. to stop the fermenting,
homogenizing the fermented recombinant microbial cells in the fermentation solution,
extracting the Semaglutide intermediate polypeptide Arg34GLP-1(9-37) (SEQ ID NO: 1) from the homogenized fermentation solution, and
digesting the extracted Semaglutide intermediate polypeptide Arg34GLP-1(9-37) (SEQ ID NO: 1) by enzymatic digestion in solution.

10. The method of claim 8, further comprising:
culturing the recombinant microbial cell in LB medium at 35° C. to 40° C. for 8 to 12 hours to obtain a pre-culture seed solution,
transferring the pre-culture seed solution to a first base fermentation medium for 8 to 12 hours to obtain a seed solution,
transferring the seed solution to a second base fermentation medium to produce a fermentation solution,
fermenting the fermentation solution until an $OD_{600}$ value of the fermentation solution reaches 100 to 200,
inducing the fermentation solution with IPTG at a concentration of 0.05 mM to 1 mM,
incubating the fermentation solution for 8 to 18 hours at 25° C. to 40° C.,
collecting the recombinant microbial cell from the fermentation solution,
homogenizing the recombinant microbial cell in solution,
extracting the recombinant microbial cell from the solution, and
digesting the recombinant microbial cell extract by enzymatic digestion.

11. The preparation method of claim 9, further comprising:
precipitating inclusion bodies (IB) by centrifuging and collecting the IBs after lysing the fermented recombinant microbial cells from the fermentation solution,
washing the IBs with a washing buffer,
dissolving the washed IBs with a dissolving buffer at a pH of 6.0 to 10.0 to produce a dissolved fusion protein with a protein concentration of 5 g/L to 55 g/L,
digesting the dissolved fusion protein by enzyme digestion with enterokinase (EK) at 30° C. to 35° C. for 20 to 24 hours to obtain a mixed solution containing an intermediate polypeptide, a fusion peptide, and a binding peptide,
purifying the mixed solution to obtain an intermediate polypeptide sample.

* * * * *